United States Patent [19]

Bodor et al.

[11] 4,313,956
[45] Feb. 2, 1982

[54] NOVEL SYPATHOMIMETIC AMINE PRODRUGS

[75] Inventors: Nicholas S. Bodor, Gainesville, Fla.; Kenneth B. Sloan, Eudora; Stefano A. Pogany, Lawrence, both of Kans.

[73] Assignee: INTERx Research Corp., Lawrence, Kans.

[21] Appl. No.: 108,055

[22] Filed: Dec. 28, 1979

[51] Int. Cl.³ ................ C07C 149/40; A61K 31/265; C07C 79/46; C07C 101/72; C07C 102/00; C07C 101/44; A61K 31/165; C07C 103/20; C07C 97/16; C09F 5/08; C07C 153/00; C07C 69/76; C07C 69/00; C07C 67/02; C07C 101/20; C07C 69/74; C07C 67/02; A61K 31/25; A61K 31/235; A61K 31/245; A61K 31/22; A61K 31/26; A61K 31/255; A61K 31/275; A61K 31/215; C07C 101/30; C07C 101/02; C07C 69/66; C07C 69/34; A61K 31/23; A61K 31/225; A61K 31/22; A61K 31/16; C07C 101/00; C07C 79/40; C07C 101/26

[52] U.S. Cl. ................ 424/301; 560/170; 260/410.5; 560/172; 424/302; 260/455 R; 424/303; 424/304; 560/106; 424/305; 424/307; 560/142; 424/308; 424/310; 560/252; 424/311; 424/312; 560/171; 424/313; 424/314; 560/9; 424/320; 424/324; 560/20; 424/156; 424/157; 560/46; 564/153; 564/154; 560/47; 564/162; 564/165; 560/251; 564/159; 564/160; 560/104; 564/168; 564/169; 560/105; 564/166; 564/167; 560/49; 564/196; 564/200; 560/50; 564/170; 564/185; 560/51; 564/212; 564/213; 560/53; 564/202; 564/207; 560/54; 564/220; 560/75; 560/85; 560/121; 560/123; 560/124; 560/125; 560/126; 560/127; 560/128; 560/152; 560/153; 560/154; 560/156; 560/169

[58] Field of Search ................ 424/177, 307, 308, 310, 424/311–314, 320, 324; 560/142, 109, 252, 219, 221, 227, 228, 1, 171, 9, 20, 46, 47, 25, 104–106, 49–51, 53, 54, 75, 85, 152–154, 156, 169–174, 176, 177, 180–188, 192, 193, 219, 221, 227, 228; 260/455, 410.5, 557 R, 558 R, 562 A

[56] References Cited

U.S. PATENT DOCUMENTS 3,164,629 1/1965 Zölss et al. .................. 560/142
3,809,714 5/1974 Hussain et al. ............... 560/142

Primary Examiner—Delbert R. Phillips
Attorney, Agent, or Firm—Michael C. Sudol, Jr.

[57] ABSTRACT

Novel, transient prodrug forms of the phenolic dihydroxy sympathomimetic amines have (i) the structural formula (I):

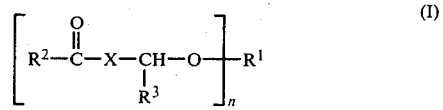

(I)

wherein X is O, S or $NR^5$; n is 1 or 2; $R^1$ is the monodehydroxylated residue of a phenolic, nuclear dihydroxy natural sympathetic or sympathomimetic amine when n is 1, and the didehydroxylated residue of a phenolic, nuclear dihydroxy natural sympathetic or sympathomimetic amine when n is 2; $R^2$ is selected from the group consisting of straight or branched chain alkyl having from 1 to 20 carbon atoms; aryl having from 6 to 10 carbon atoms; cycloalkyl having from 3 to 8 carbon atoms; alkenyl having from 2 to 20 carbon atoms; cycloalkenyl having from 4 to 8 carbon atoms; alkynyl having from 2 to 20 carbon atoms; aralkyl, alkaryl, aralkenyl, aralkynyl, alkenylaryl, alkynylaryl, loweracyloxyalkyl, and carboxyalkyl, wherein alkyl, aryl, alkenyl and alkynyl are as defined above; saturated or unsaturated monoheterocyclic or polyheterocyclic, or fused heterocyclic, containing from 1 to 3 of any one or more of the hetero atoms N, S or O in each heterocyclic ring thereof and each such ring being from 3- to 8-membered; and mono-or poly-substituted derivatives of the above, each of said substituents being selected from the group consisting of lower alkyl, lower alkoxy, lower acyl, lower acyloxy, halo, haloloweralkyl, cyano, carbethoxy, loweralkylthio, amino, nitro, loweralkylamino, diloweralkylamino, carboxyl, carbamyl, loweralkylcarbamyl, diloweralkylcarbamyl and

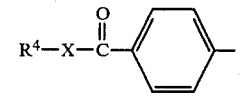

wherein $R^4$ is hydrogen or alkyl having from 1 to 10 carbons; $R^3$ is hydrogen, $R^2$, lower acyl, cyano, haloloweralkyl, carbamyl, loweralkylcarbamyl, diloweralkylcarbamyl, —CH$_2$ONO$_2$ and —CH$_2$OCOR$^2$; $R^5$ is hydrogen or lower alkyl; (ii) the structural formula (II):

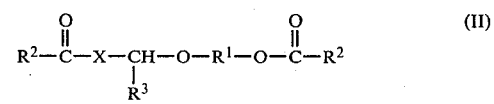

(II)

wherein X, $R^2$ and $R^3$ are as defined above and $R^1$ is the didehydroxylated residue of a phenolic, nuclear dihydroxy natural sympathetic or sympathomimetic amine; (iii) either of the structural formulae (I) or (II) wherein

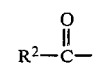

is the residue of any naturally occurring protein amino acid, the residue of any N-substituted naturally occurring amino acid, which N-substituent is lower alkyl or any amino acid protective group cleavable via hydrogenolysis or hydrolysis, or the residue of an N, N-lower dialkyl or $C_4$–$C_7$ cycloalkylamino acid; and (iv) the non-toxic, pharmaceutically acceptable salts thereof.

36 Claims, No Drawings

NOVEL SYPATHOMIMETIC AMINE PRODRUGS

BACKGROUND OF THE INVENTION

1. Field of the Invention

The present invention relates to novel, transient prodrug derivatives of the biologically active, phenolic dihydroxy natural sympathetic or sympathomimetic amines, and, more especially, relates to certain acyl-X-methylether latentiated forms of such amines, e.g., of the catecholethylamines.

As employed in this application, the expression "prodrug" denotes a derivative of a known and proven prior art compound, which derivative, when absorbed into the bloodstream of a warm-blooded animal, "cleaves" in such a manner as to release the proven drug form and permits the same to attain a higher bioavailability level than that which could be obtained if the proven drug form, per se, was administered.

Furthermore, also as used in this application, the term "transient" denotes "cleavage" of the compounds of this invention in such a manner that the proven drug form is released and the remaining "cleaved" moiety is non-toxic and metabolized in such a manner that non-toxic, metabolic products are produced.

2. Description of the Prior Art

It is well known to this art that the phenolic dihydroxy natural sympathetic or sympathomimetic amines and their salts [hereinafter simply the "synpathomimetic amines"], e.g., epinephrine, norepinephrine, isoproterenol, isoetharine, protochylol, adrenalone, dihydroxyphenylaminobutanol, nordefrin, colterol, fenoterol, metaproterenol, terbutaline, carbidopa, methyldopa, etc., are useful active agents for the treatment or management of a wide variety of disease states or conditions, e.g., glaucoma, inflammation, itching, asthma, nasal congestion, allergic states, bronchospasm, cardiac dysfunction, bronchial constriction, peripheral vascular disease, shock, and the like. See generally Cutting's *Handbook of Pharmacology*, 41, "Sympathetic Stimulants or Adrenergic Agents", pp. 436-455, Sixth Edition (1979).

Nevertheless, it too is well known to the art that such sympathomimetic amines, and the various art-recognized therapeutically active derivatives thereof, are characterized by certain inherent disadvantages, notably serious bioavailability and physiological availability problems upon administration. Such reduced availability can be attributed in part to poor lipid solubility [by reason of the presence of the hydrophilic phenolic hydroxyl groups], and also to metabolic losses during and following conventional administration. Other disadvantages associated with the prior art compounds are instability to both air and light, and same are subject to chemical attack by many agents that are conventionally used in pharmaceutical preparations, as well as a variety of other unfavorable pharmacodynamic properties. Also, for certain applications, e.g., to elicit a topical anti-inflammatory response, relatively high concentrations of drug are required.

Thus, there exists a clear and present need for novel latentiated forms of the sympathomimetic amines, which derivatives would be conspicuously devoid of those disadvantages and drawbacks that to date have characterized the prior art compounds.

SUMMARY OF THE INVENTION

Accordingly, a major object of the present invention is the provision of a novel class of synpathomimetic amine prodrugs.

Another object of this invention is the provision of a novel class of sympathomimetic amine prodrugs that is essentially free from the unwanted effects associated with the prior art.

Still another object of the invention is to provide a new and useful class of latentiated sympathomimetic amines which is characterized by enhanced stability and solubility, can be administered in standard pharmaceutical formulations to warm-blooded animals to elicit a local, topical or systemic physiological or pharmacological beneficial effect, and which exhibits enhanced bioavailability and physiological availability.

Yet another object is to provide a novel class of sympathomimetic amine prodrugs which will elicit a more effective sympathomimetic response, at lower concentrations or dosage levels, than its parent molecules.

Other objects, features and advantages of the invention will be apparent to those skilled in the art from the detailed description of the invention which follows.

DETAILED DESCRIPTION OF THE INVENTION

More particularly according to this invention, all of the aforenoted objects, features and advantages thereof are provided by the novel sympathomimetic amine (i) prodrugs having the structural formula (I):

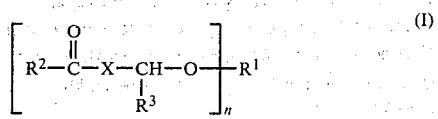

wherein X is O, S or $NR^5$; n is 1 or 2; $R^1$ is the monodehydroxylated residue of a phenolic, nuclear dihydroxy natural sympathetic or sympathomimetic amine when n is 1, and the didehydroxylated residue of a phenolic, nuclear dihydroxy natural sympathetic or sympathomimetic amine when n is 2; $R^2$ is selected from the group consisting of straight or branched chain alkyl having from 1 to 20 carbon atoms; aryl having from 6 to 10 carbon atoms; cycloalkyl having from 3 to 8 carbon atoms; alkenyl having from 2 to 20 carbon atoms; cycloalkenyl having from 4 to 8 carbon atoms; alkynyl having from 2 to 20 carbon atoms; aralkyl, alkaryl, aralkenyl, aralkynyl, alkenylaryl, alkynylaryl, loweracyloxyalkyl, and carboxyalkyl, wherein alkyl, aryl, alkenyl and alkynyl are as defined above; saturated or unsaturated monoheterocyclic or polyheterocyclic, or fused heterocyclic, containing from 1 to 3 of any one or more of the hetero atoms N, S or O in each heterocyclic ring thereof and each such ring being from 3- to 8-membered; and mono- or poly-substituted derivatives of the above, each of said substituents being selected from the group consisting of lower alkyl, lower alkoxy, lower acyl, lower acyloxy, halo, haloloweralkyl, cyano, carbethoxy, loweralkylthio, amino, nitro, loweralkylamino, diloweralkylamino, carboxyl, carbamyl, loweralkylcarbamyl, diloweralkylcarbamyl and

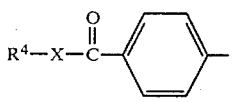

wherein $R^4$ is hydrogen or alkyl having from 1 to 10 carbons; $R^3$ is hydrogen, $R^2$, lower acyl, cyano, halo-loweralkyl, carbamyl, loweralkylcarbamyl, diloweralkylcarbamyl, —$CH_2ONO_2$ and —$CH_2OCOR^2$; $R^5$ is hydrogen or lower alkyl; (ii) prodrugs having the structural formula (II):

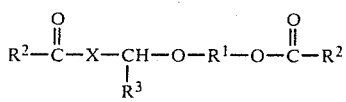
(II)

wherein X, $R^2$ and $R^3$ are as defined above and $R^1$ is the didehydroxylated residue of a phenolic, nuclear dihydroxy natural sympathetic or sympathomimetic amine; (iii) prodrugs having either the structural formulae (I) or (II) wherein

is the residue of any naturally occurring protein amino acid, the residue of any N-substituted naturally occurring amino acid, which N-substituent is lower alkyl or any amino acid protective group cleavable via hydrogenolysis or hydrolysis (e.g., formyl, benzyloxy, carbonyl, t-butyloxycarbonyl), or the residue of an N,N-lowerdialkyl or $C_4$-$C_7$ cycloalkylamino acod; and (iv) the non-toxic, pharmaceutically acceptable salts thereof.

By "monodehydroxylated" residue of a phenolic, nuclear dihydroxy natural sympathetic or sympathomimetic amine as utilized herein, there are intended those monovalent radicals as would result upon removal of one of the phenolic hydroxyls from the nucleus of the parent aromatic sympathomimetic amine and leaving a free or unsatisfied valence bond in its stead, i.e., that valence bond which defines the bridge to the $R^2COXCH(R^3)O$ moiety of the compounds of the structural formula (I). Similarly, the "didehydroxylated" residue connotes those divalent radicals as would result upon removal of both nuclear hydroxyls. Thus, representative monovalent radicals include, for example:

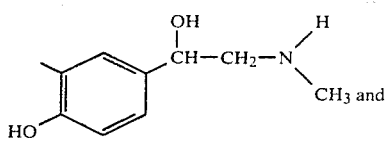

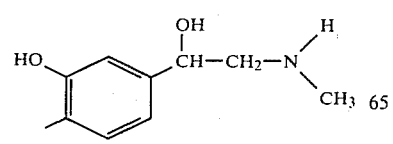

[epinephrine residues]

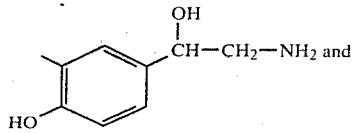

[norepinephrine residues]

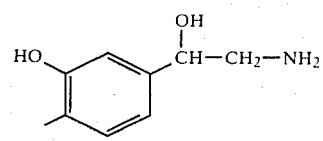

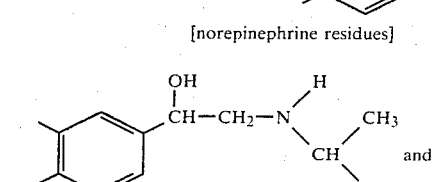

[isoproterenol residues]

and representative divalent radicals correspondingly include:

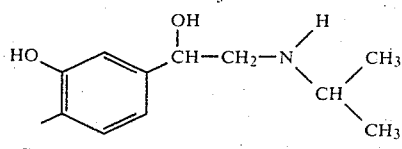

[epinephrine residue]

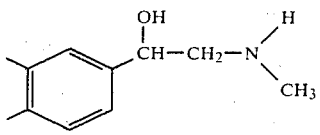

[norepinephrine residue]

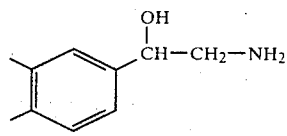

[isoproterenol residue]

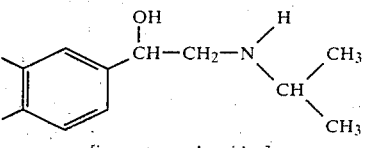

[metaproterenol residue]

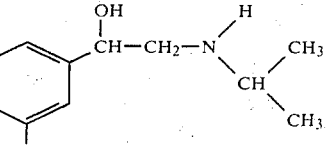

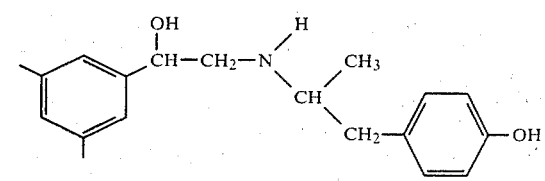

[fenoterol residue]

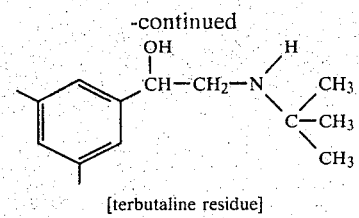

[terbutaline residue]

The term "naturally occurring protein amino acid" includes without limitation:

Glycine
Alanine
Valine
Leucine
Isoleucine
Cysteine
Cystine
Methionine
Serine
Threonine
Aspartic Acid
Glutamic acid
Arginine
Lysine
Hydroxylsine
Phenylalanine
Tyrosine
Asparagine
Glutamine
Proline
Hydroxyproline
Histidine
Tryptophan
Pyroglutamic acid Similarly, the import of the phrase "amino acid protective group 'cleavable' via hydrogenolysis or hydrolysis" can be further gained from a review of U.S. Pat. No. 3,803,102 to Felix and U.S. Pat. No. 3,957,803 to Bodor, et al.

It too will be appreciated that by "residue" of a naturally occurring amino acid there are intended not only those species wherein the "CO" of the $R^2$—CO— moiety comprising the topic prodrugs is the carbonyl function originating from the amino acid, per se, e.g., species of the type

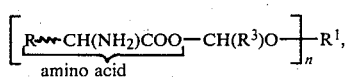

but also such species including a free carboxyl function, e.g., species of the type

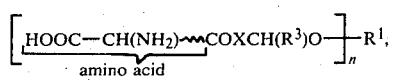

as well as amino acid species of amido type, wherein the —$CONHR^5$ function comprises the parent amino acid, e.g., species of the type

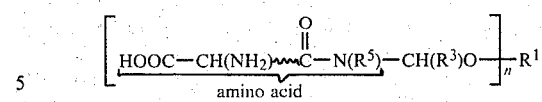

When $R^2$ comprises a heterocyclic function, representative such heterocycles include, without limitation, and without regard to the point of attachment on the ring, piperazinyl, 4-methylpiperazinyl, pyridinyl, pyrazinyl, pyrimidinyl, pyridazinyl, pyrazolyl, pyrrolyl, pyrrolidinyl, pyrrolinyl, pyrazolinyl, pyrazolidinyl, piperidyl, morpholinyl, quinuclidinyl, isoindolinyl, indolinyl, thienyl, benzothienyl, napthothienyl, thianthrenyl, furyl, pyranyl, chromenyl, xanthenyl, phenoxathiinyl, imidazolyl, pyridyl, indolizinyl, isoindolyl, 3H-indolyl, indolyl, indazolyl, purinyl, phthalazinyl, quinolyl, isoquinolyl, 4H-quinolizinyl, quinoxalinyl, naphthyridinyl, cinnolinyl, pteridinyl, carbazolyl, 4aH-carbazolyl, β-carbolinyl, phenanthridinyl, acridinyl, perimidinyl, phenoxazinyl, furazanyl, isochromanyl, chromanyl, imidazolinyl, 1-methyl-azarinyl, 1-methyl-pyrrolyl, 1-methyl-imidazolyl, 1-methyl-pyrazolyl, 2-methyl-isoindolyl, 3H-indolyl, phthalazinyl, quinoxilinyl, quinazidinyl, phenazinyl, isothiazolyl, 10-methyl-phenothiazinyl, isoxazolyl, furazanyl, the various saturated, unsaturated or partially saturated congeners of any of the above, and those attached to the carbonyl carbon via a lower alkylene bridge.

By "pharmaceutically acceptable salt", there are intended the conventional non-toxic salts or the quaternary ammonium salts of the compounds of the formulae (I) and (II), formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, fumaric, toluenesulfonic, and the like.

The pharmaceutically acceptable salts of the present invention can be synthesized from the compounds embraced by formulae (I) and (II) by conventional chemical methods. Generally, the salts are prepared by reacting the free base with stoichiometric amounts or with an excess of the desired salt forming inorganic or organic acid in a suitable solvent or various combination of solvents. For example, the free base can be dissolved in a mixed aqueous solution of the appropriate acid and the salt recovered by standard techniques, for example, by evaporation of the solution. Alternatively, the free base can be charged into an organic solvent such as a lower alkanol, a symmetrical or asymmetrical ether containing 2 to 10 carbon atoms, an alkyl ester, or mixtures thereof, and the like, and then it is treated with the appropriate acid to form the corresponding salt. The salt is recovered by standard recovery techniques, for example, by filtration of the desired salt or spontaneous separation from the solution, or it can be precipitated by the addition of a solvent in which the salt is insoluble and recovered therefrom.

Examples of suitable inorganic and organic solvents for performing the various reactions include any inorganic or organic solvent that does not adversely affect the reactants or the resulting product, including halogenated solvents such as methylene chloride, chloroform, carbon tetrachloride, ethylene chloride, ether solvents such as diethyl ether, dimethyl ether, and other solvents such as tetrahydrofuran, dioxane, diglyme, n-hexane, cyclooctane, benzene, heptane, cyclohexane, mixtures thereof, and like aliphatic, cycloaliphatic and aromatic hydrocarbon solvents, water, acidified aqueous solutions, mixed organic and inorganic solutions, ethyl acetate, propyl acetate, and the like.

The "quaternary ammonium salts" are likewise conventional to the pharmaceutical arts, and these too are prepared via typical methodology. Moreover, either the $R^1$ or the $R^2$ moiety, or both, of the subject prodrug molecules can be quaternized or otherwise comprise a salt function.

The compounds of the present invention are conveniently prepared via the following general syntheses:

SYNTHETIC SCHEME "A"

In a first step, the amine function of the sympathomimetic amine, e.g., epinephrine, is suitably protected, e.g., with a t-butyloxycarbonyl protective group by reaction with t-butylazidoformate, in the presence of base, e.g., triethylamine or N-methylmorpholine, in a polar aprotic solvent, e.g., dioxane, THF or dichloromethane, under atomspheric pressure and at a temperature of from −20° C. to the boiling point of the solvent, preferably from 0° C. to 20° C. Next, the N-t-butoxycarbonyl epinephrine which results is reacted, under $S_N{}^2$ conditions, with 2-4 equivalents of a compound of the formula:

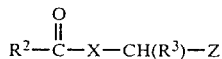

wherein X, $R^2$ and $R^3$ are as above defined and Z is suitable leaving group, e.g., chloride, bromide, tosylate, etc., and preferably the iodide, in the presence of 2-4 equivalents of e.g., potassium carbonate in a ketone solvent, e.g., acetone, methylethylketone, cyclohexanone, 2-pentanone, 3-hexanone, or the like, to form a compound having the structural formula:

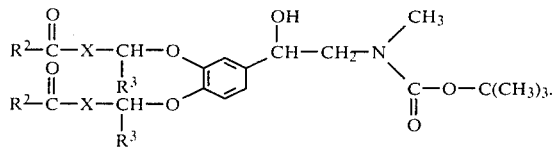

The t-BOC protective group is thence removed by protonation with HA, e.g., with HCl in ethyl acetate, or trifluoroacetic acid in dichloromethane or tetrahydrofuran, or any "other" common reagent for removing the t-BOC protective group in amino acid chemistry, to result in the compound according to the invention:

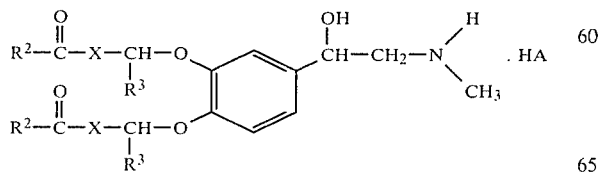

from which the monoacyl-X-methylether derivative, namely:

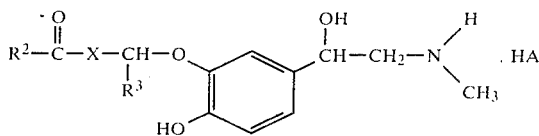

or the other isomeric form, or a mixture of both isomeric forms, may be prepared, via simple partial hydrolysis.

The reactant

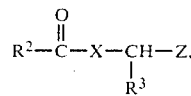

wherein X is either O, S or $NR^5$, is prepared thus:

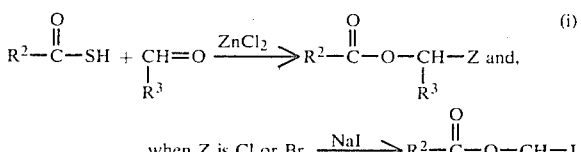

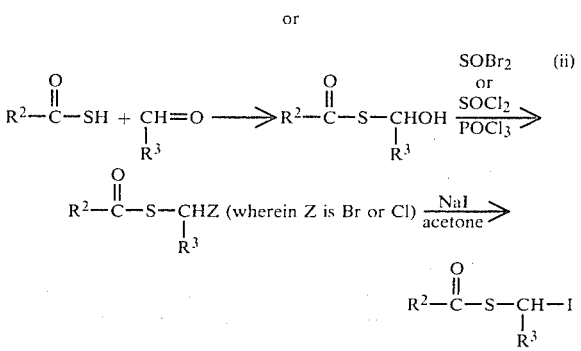

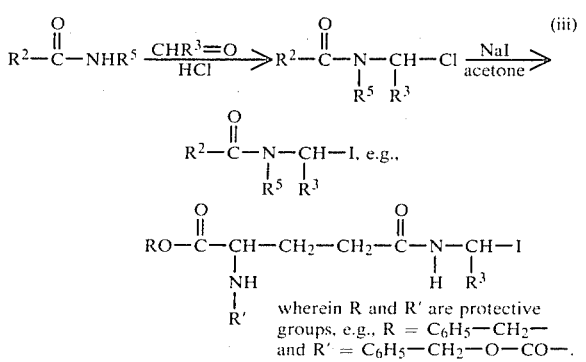

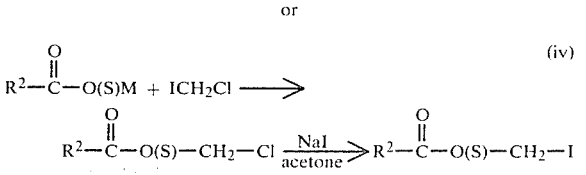

or

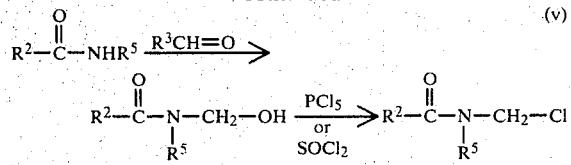

the like. Similarly, the benzyl hydroxyl function too may be protected, e.g., by lower acylation. The N-protected or O-protected compounds, thus, not only are useful intermediates, but are also useful final products, also demonstrating the utility of the patent drug species.

A representative synthetic Scheme "A", thus, would include:

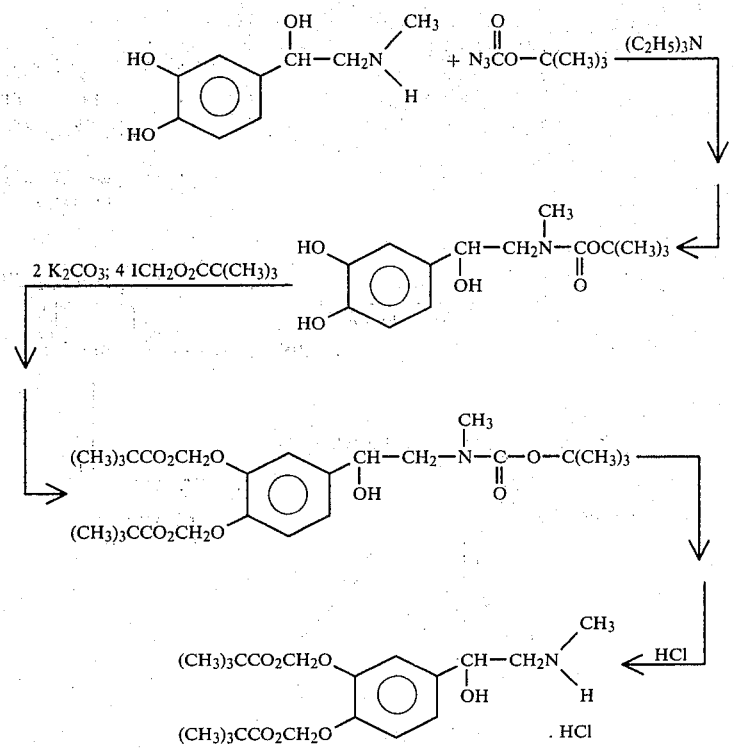

Other suitable N-protective groups, i.e., other than t-butoxycarbonyl or t-BOC protective group, include N-formate, carbobenzyloxy, —CH$_2$—S—R, —COCF$_3$, —C(CH$_3$)=C=COCH$_3$, any completely protected peptide, e.g., —CO—CH(R)NHCH=O, =CH—C$_6$H$_4$(m-OH) [for, e.g., norepinephrine], and

SYNTHETIC SCHEME "B"

Depending on whether $S_N{}^1$ or $S_N{}^2$ conditions are employed, both the diacyl-X-methylether derivatives, or the half acylated, half acyl-X-methylated derivatives, or isomers, may be prepared from an aldehyde starting material, thus:

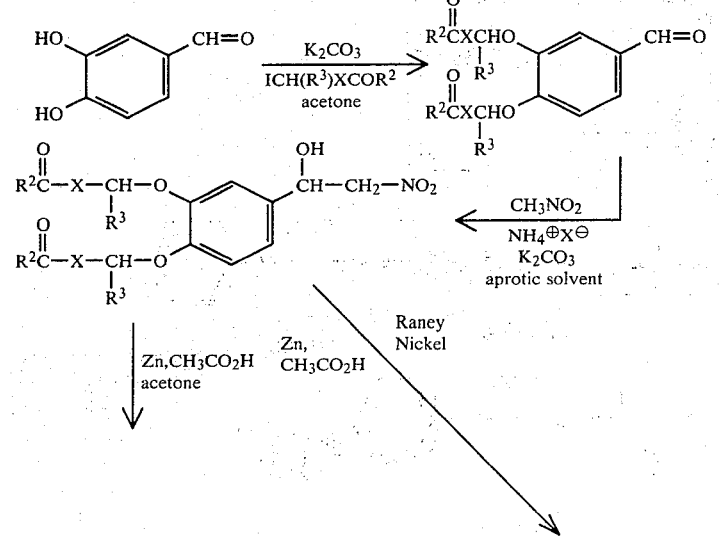

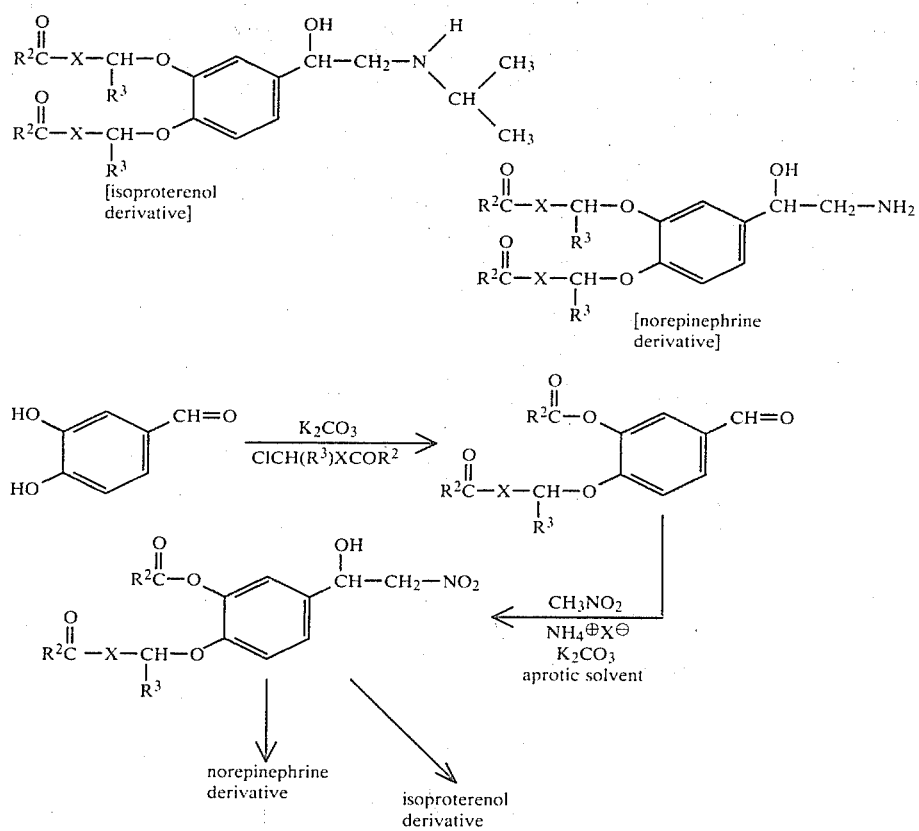
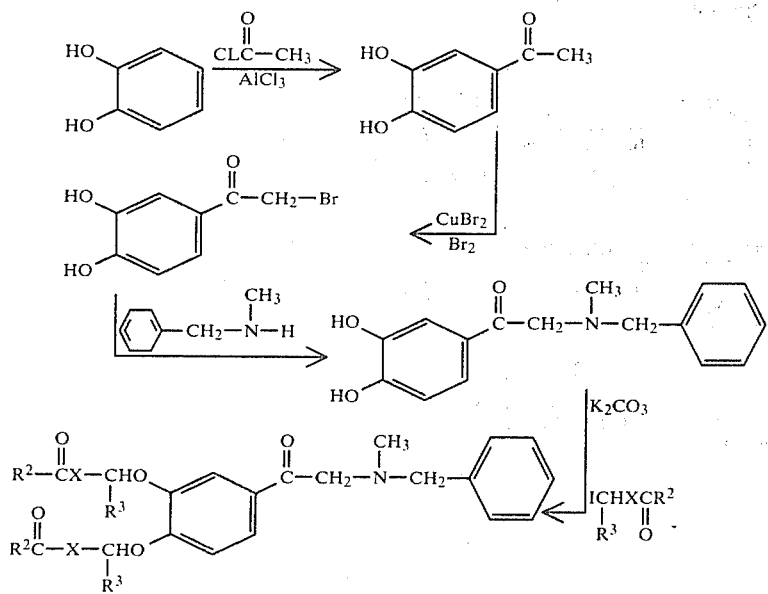
SYNTHETIC SCHEME "C"
An alternative route to the epinephrine derivatives, and to the adrenalones, proceeds as follows:

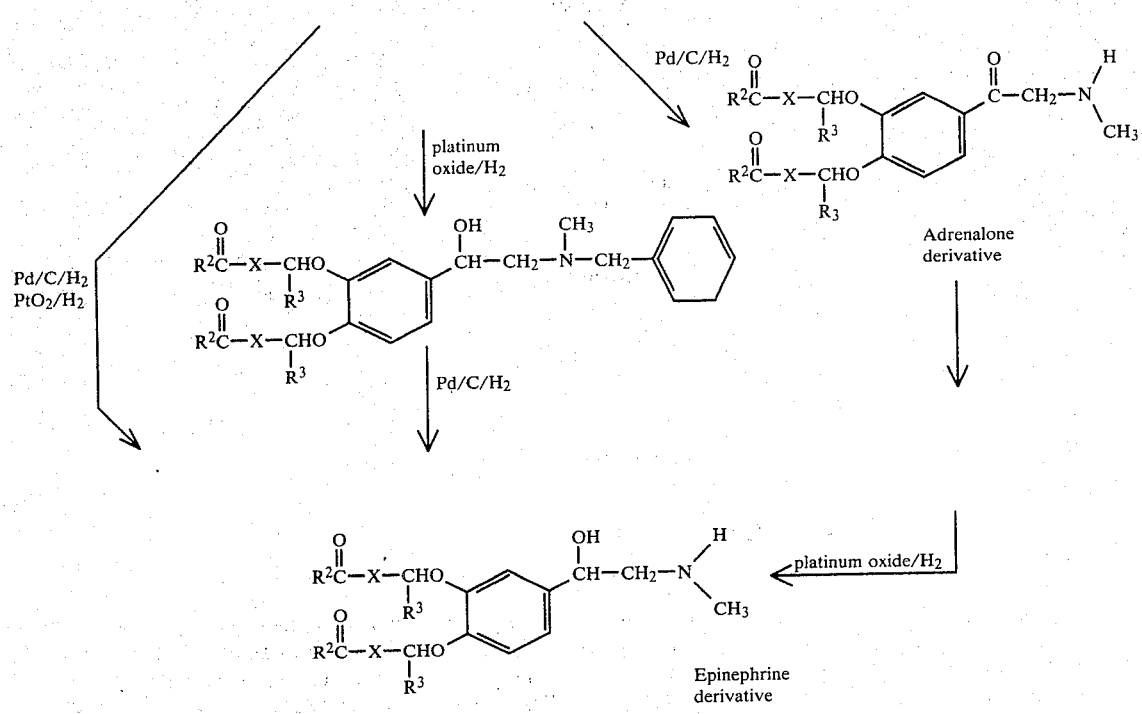
SYNTHETIC SCHEME "D"
Another alternate route, utilizing the adrenalones as starting materials, is as follows:
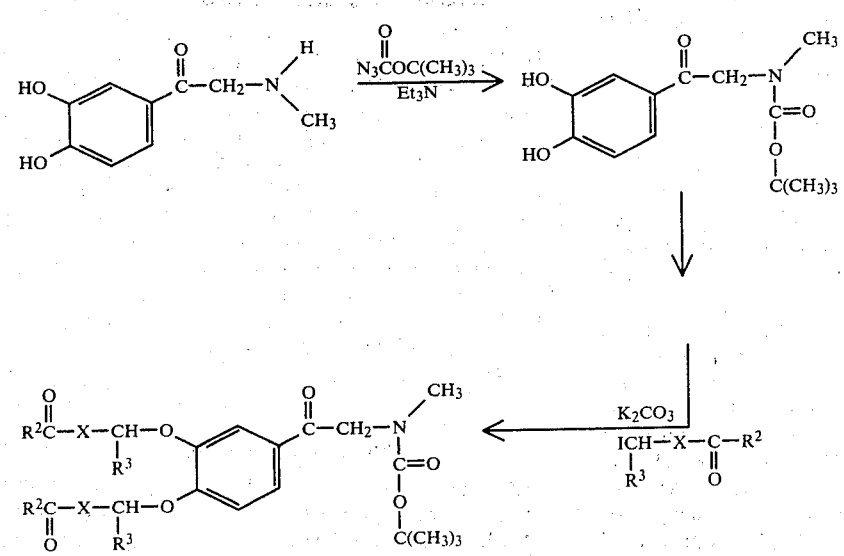

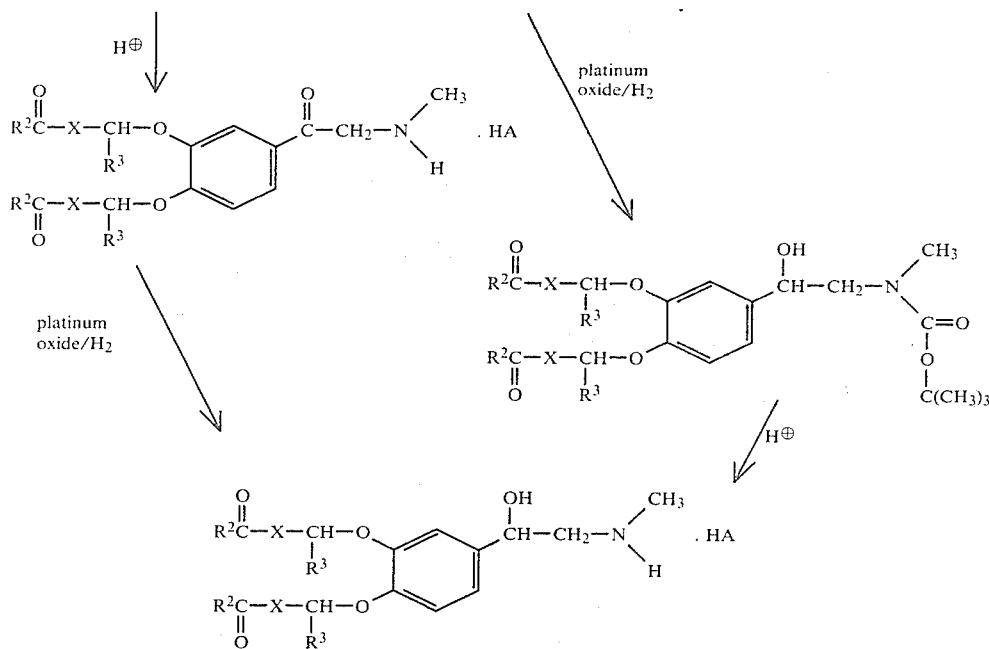

While all of the compounds according to the invention are characterized by good lipid solubility and high bioavailability, are quite stable to both air and light, and are more immune to chemical attack by those agents which are conventionally used in pharmaceutical preparations, the same are nonetheless facilely chemically and/or enzymatically metabolized/hydrolyzed at their therapeutic sites of action, i.e., upon administration are cleaved into the known and proven parent drug molecule, e.g., epinephrine, per se, as well as into various non-toxic products of metabolism/hydrolysis, according to the following general scheme:

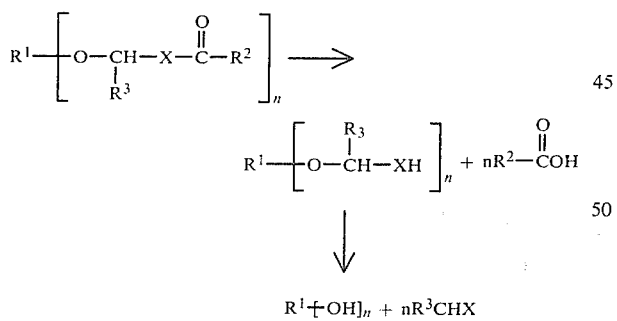

It will be appreciated that it is a critical feature of the present invention that the ether oxygen and the X function comprising the acyl-X-methylether moiety of the subject prodrug compounds be separated by but a single carbon atom or methylene bridge. Otherwise, e.g., if the "methylene" linkage were ethylene or higher alkylene, such compounds would not be subject to the aforesaid chemical and/or enzymatic metabolism/hydrolysis and would not be facilely cleaved in vivo, into the noted non-toxic products of metabolism/hydrolysis. Hence, such ethylene and higher alkylene congeners are inoperative and not intended herein; indeed, same could not properly be deemed or designated as true "prodrugs".

While all of the compounds encompassed within the aforesaid generic formulae (I) and (II) meet applicants' criteria, nevertheless certain compounds remain preferred, namely, the dipivalyloxymethyl, dihexanoyloxymethyl, diheptanoyloxymethyl, dioctanoyloxymethyl, di-n-dodecanoyloxymethyl, di-n-tetradecanoyloxymethyl, di-n-hexadecanoyloxymethyl, diacetyloxymethyl, dipentanoyloxymethyl, dibenzoyloxymethyl, dibenzoyloxybenzyl, dipropionyloxymethyl, dibutyryloxymethyl, benzoylaminomethyl, pivalylthiomethyl and dimethylaminoacetylaminomethyl derivatives of epinephrine, nonepinephrine and isoproterenol.

In order to further illustrate the present invention and the advantages thereof, the following specific examples are given, it being understood that same are intended only as illustrative and in nowise limitative.

EXAMPLE 1

3-Pivalyloxy-4-pivalyloxymethoxybenzaldehyde 3,4-Dihydroxybenzaldehyde (27.6 g, 0.2 mol) was dissolved in 100 mL of DMF with 45 mL of triethylamine and 40 mL of pivalyloxymethyl chloride. The mixture was stirred at room temperature for five days. After one day 20 mL of pivalyloxymethyl chloride and 20 ml of triethylamine were added to the mixture. The mixture was then poured into 600 mL of water. The water was extracted with 600 mL of $CH_2Cl_2$ and twice with 500 mL of ether. The organic layers were concentrated and that residue was chromatographed on silicAr CC-7 using petroleum ether bp 30°-60°, acetone (1:1) as the eluent to give the desired compound: mp 58°-60°.

Anal. Calcd for $C_7H_6O_3$: C, 64.27; H, 7.19. Found: C, 64.04; H, 7.26.

EXAMPLE 2

N-t-Butoxycarbonyl epinephrine

A slurry of 18.3 g (0.10 mol) epinephrine, 14.3 g (0.10 mol) t-butylazidoformate and 13.9 mL triethylamine in 25 mL pyridine was heated under nitrogen to 70° for 24 hr. The solvent was removed and the residue dissolved in ether. The ether was washed with 10% HCl, saturated NaHCO$_3$, H$_2$O, saturated NaCl and dried (MgSO$_4$). The solvent was evaporated to give 14.6 g of a viscous brown oil which was suitable for reaction without further purification: IR (CHCl$_3$) 3560 (—OH), 3480 (—OH), 1660 cm$^{-1}$ (C=O); NMR (CDCl$_3$) 1.38 (s, 9H, —C(CH$_3$)$_3$, 2.72 (s, 3H, —N—CH$_3$), 3.30 (broad s, 2H, —CH$_2$—N), 4.67 (broad t, 1H, CH—OH), 6.73 (d, 3H, aromatic).

EXAMPLE 3

N-t-Butoxycarbonyl-3,4-dihexanoyloxymethyl epinephrine

A mixture of N-t-butoxycarbonyl epinephrine (5.2 g, 0.019 mol) and potassium carbonate (7.9 g, 0.057 mol) in 100 ml dry acetone was stirred under nitrogen and cooled in an ice bath. A solution of 10.7 g (0.042 mol) iodomethyl hexanoate in 50 mL dry acetone was added dropwise to the mixture over 15 min. The mixture was stirred at ice bath temperature for 60 min. following completion of addition and filtered. The solvent was evaporated and the residue was chromatographed on a small column containing 40 g of silica (Mallinckrodt CC-7). The column was eluted with 2 column volumes of petroleum ether (30°–60°) which were discarded and the product was eluted with 3 column volumes of ethyl acetate. The solvent was removed and product was purified by low pressure chromatography using 25% acetone/hexane to give 5.9 g (57%) of a pale yellow oil: IR (CHCl$_3$) 3400 (—OH), 1750 (—CO$_2$R), 1675 cm$^{-1}$ (NCO$_2$R); NMR (CDCl$_3$)

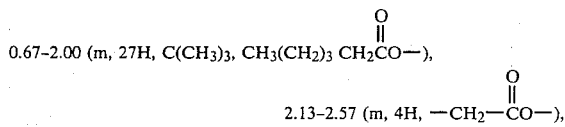

0.67–2.00 (m, 27H, C(CH$_3$)$_3$, CH$_3$(CH$_2$)$_3$ CH$_2$CO—), 2.13–2.57 (m, 4H, —CH$_2$—CO—), 2.83 (s, 3H, —N—CH$_3$), 3.40 (d, 2H, —CH$_2$—N—),

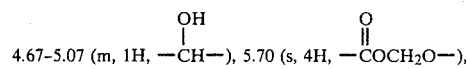

4.67–5.07 (m, 1H, —CH—), 5.70 (s, 4H, —COCH$_2$O—), 7.10 (d, 3H, aromatic).

Anal. Calcd for C$_{28}$H$_{45}$NO$_9$: C, 62.31; H, 8.41; N, 2.66. Found: C, 62.75; H, 8.72; N, 2.66.

EXAMPLE 4

N-t-Butoxycarbonyl-3,4-dipivalyloxymethyl epinephrine

To a mixture of 5.2 g (0.019 mol) N-t-butoxycarbonyl epinephrine and 5.8 g (0.042 mol) potassium carbonate in 100 mL dry acetone was added 10.1 g (0.042 mol) iodomethyl pivalate. The reaction was stirred under nitrogen overnight and filtered. The solvent was evaporated and the residue was chromatographed in a small column containing 40 g of silica. The column was eluted with 2 column volumes of petroleum ether which were discarded and the product was eluted with 3 column volumes of ethyl acetate. The solvent was removed and the product was purified by low pressure chromatography using 25% acetone/hexane to give 5.2 g (55%) of a yellow oil; IR (CHCl$_3$) 3600 (OH), 3410 (—OH), 1740 (—CO$_2$r), 1680 cm$^{-1}$ (—NCO$_2$R); NMR (CDCl$_3$ 1.22 (s, 18H, (CH$_3$)$_3$CO$_2$—), 1.50 (s, 9H, (CH$_3$)$_3$COC=O), 2.80 (s, 3H, —N—CH$_3$), 3.42 (d, 2H, —CH$_2$—N—), 4.87 (m, 1H, CH—OH), 5.73 (s, 4H, O=C—O—CH$_2$—O), 7.08 (d, 3H, aromatic).

Anal. Calcd for C$_{26}$H$_{41}$NO$_9$: C, 61.04; H, 8.08; N, 2.74. Found: C, 61.18; H, 8.13; N, 2.72.

EXAMPLE 5

3,4-O-Dipivalyloxymethylepinephrine hydrochloride

N-t-Butoxycarbonyl-3,4-O-dipivalyloxymethylenepinephrine (0.288 g, 0.56 mmol) dissolved in ethyl acetate (10 mL) was bubbled anhydrous hydrogen chloride for 5 min. at 0°. The excess acid and solvent were removed in vacuo to yield 0.25 g of a clear syrup NMR (acetone-d$_6$) 1.16 (s, 18H, (CH$_3$)$_3$C—), 2.86 (broad, 3H, N—CH$_3$), 3.30 (s, 2H, —CH$_2$—N—), 5.30 (broad, 1H, —CH—O), 5.76 (s, 4H, OCH$_2$O), 7.15 (broad, 3H, Ar—H); IR (film) 3300 cm$^{-1}$ (broad), 2290 cm$^{-1}$, 1750 cm$^{-1}$ (C=O).

Anal. Calcd for C$_{21}$H$_{34}$NO$_7$Cl: N, 3.12; C, 56.30; H, 7.66. Found: N, 3.10; C, 55.80; H, 7.65.

EXAMPLE 6

3,4-Dihydroxybenzaldehyde-bis-pivalyloxymethyl ether

To a solution of 1 g (7.24 mol) of 3,4-dihydroxybenzaldehyde in 40 mol of acetone, was added 3.99 g (28.9 mmol) of potassium carbonate and 2 ml of hexamethylphosphoric triamide and the mixture was stirred for 5 min. In a separate flask were combined 4.56 g (30.4 mmol) of sodium iodide and 4.37 g (29 mmol) of chloromethylpivalate in 50 ml of acetone. The halide exchange was allowed to proceed for 20 min. The iodomethylpivalate was transferred via pipette to the flask containing the dihydroxy compound and the potassium carbonate. After 18 hrs. tlc analysis (10% ethyl acetate/chloroform) showed total disappearance of starting material. The acetone was evaporated and replaced with ether which, after filtration of the insoluble residue was washed with water (2 × 10 ml), with brine (1 × 10 ml), dried (Na$_2$SO$_4$) and evaporated. The residual yellow oil was chromatographed on silica gel (5% ethyl acetate/chloroform) to afford 1.6 g (60%) of the desired product as an orange syrup: nmr (CDCl$_3$) 9.91 (s, 1H, CHO), 7.55–7.25 (m, 3H, aromatic), 6.88 (s, 2H, OCH$_2$O), 6.82 (s, 2H, OCH$_2$O), 1.27 (s, 18H, t-butyl); MS m/e 366 (M+).

Anal. Calcd for C$_{19}$H$_{26}$O$_7$: C, 62.29; H, 7.10. Found: C, 61.95; H, 7.08.

The following compounds are also prepared utilizing those techniques above outlined:

TABLE I $$\left[ R^2-\overset{O}{\underset{\|}{C}}-X-\underset{R^3}{\overset{|}{CH}}-O- \right]_2 R^1$$

| Ex. | R$^1$ residue | R$^2$ | R$^3$ | X |
|---|---|---|---|---|
| 7 | norepinephrine | —C(CH$_3$)$_3$ | H | O |

TABLE I-continued $$\left[ R^2-\overset{O}{\underset{\|}{C}}-X-\underset{\underset{R^3}{|}}{CH}-O \right]_2 R^1$$

| Ex. | R¹ residue | R² | R³ | X |
|---|---|---|---|---|
| 8 | isoproterenol | —C(CH₃)₃ | H | O |
| 9 | epinephrine | —C(CH₃)₃ | H | S |
| 10 | epinephrine | phenyl | H | O |
| 11 | epinephrine | phenyl | phenyl | O |
| 12 | epinephrine | —C(CH₃)₃ | —CH₃ | O |
| 13 | adrenalone | H₃C(CH₂)— | H | O |
| 14 | nordefrin | —C(CH₃)₃ | H | O |
| 15 | colterol | phenyl | —CH₃ | S |
| 16 | terbutaline | H₃C(CH₂)₅— | cyclohexyl | O |
| 17 | metaproterenol | phenyl-CH=CH₂— | —CF₃ | S |
| 18 | epinephrine | —C(CH₃)₃ | H | NH |
| 19 | fenoterol | phenyl | —C₂H₅ | S |
| 20 | norepinephrine | cyclohexyl | phenyl | NH |
| 21 | isoetharine | piperazinyl | —CH₃ | O |
| 22 | adrenalone | morpholinyl | —CH₃ | O |
| 23 | epinephrine | —C₁₂H₂₅ | H | S |
| 24 | norepinephrine | —C₅H₁₁ | —CCl₃ | O |
| 25 | epinephrine | —CH₃ | —CH₃ | S |
| 26 | epinephrine | —CH₂—NH₂ | —CH₃ | O |
| 27 | isoproterenol | —CH(NH₂)—CH₃ | H | O |
| 28 | epinephrine | —CH₂—CH₂—CH(NH₂)COOH | CF₃ | NH |
| 29 | epinephrine | —CH(NH—C(=O)—O—CH₂—C₆H₅)—CH₂—C₆H₅ | H | O |

TABLE II $$R^2-\overset{O}{\underset{\|}{C}}-X-\underset{\underset{R^3}{|}}{CH}-O-R^1-O-\overset{O}{\underset{\|}{C}}-R^2$$

| Ex. | R¹ residue | R² | R³ | X |
|---|---|---|---|---|
| 30 | epinephrine | —C(CH₃)₃ | H | O |
| 31 | norepinephrine | —C₁₂H₂₅ | H | S |
| 32 | isoproterenol | —C₁₂H₂₅ | —CH₃ | O |
| 33 | adrenalone | phenyl | H | O |
| 34 | epinephrine | —C(CH₃)₃ | cyclohexyl | O |

EXAMPLE 31

The anti-inflammatory activity of dipivalyloxymethylepinephrine (DDME), a novel prodrug according to this invention, was determined in an ear burn model vis-a-vis the known epinephrine prodrug, dipivalylepinephrine (DPE). Three different ear burn experiments were carried out, each experiment developing a comparison at two different drug dosages. The procedure of the ear burn experiments follows, as does the actual data generated.

Table III and the data, Table IV, reflect the results of the aforenoted experiments. The highest drug concentration employed ($3 \times 10^{-2}$ M) apparently contributed to the inflammatory response. The apparent inflammatory effect at high drug concentration is consistent with clinical observations in which a psoriatic response was often observed with comparable concentrations of dipivalylepinephrine (DPE).

The dose response profiles of both compounds at low concentrations indicate that DPME is 10–30 fold more effective as an anti-inflammatory agent from a dosage standpoint. Also, at low concentration levels, DPME consistently elicits a greater anti-inflammatory effect than DPE. Therefore, DPME is well suited as a topical anti-inflammatory useful for treating psoriasis, urticaria, dermatoses and the like.

Experimental Methods

Ear Burn Test

A controlled thermal challenge was administered to the right ear of female Sprague-Dawley rats, 40–60 g. The hot probe consists of two circular flat surfaces (10 mm diameter) heated to $50.40° C. \pm 0.02°$. Pressure applied during the 21 second burn administration was ca. 640 g/cm². Two groups, with and without application of vehicle (90% acetone, 10% isopropyl-myristate) served as controls. Vehicle with or without drug was applied to the right ear immediately after burning in the amount of 50 l. Rats were killed by cervical disclocation 16–18 hours after treatment and the thickness of each ear was determined with a micrometer (in inches $\times 10^3$). Burn response values were normalized by expression of the % increase in thickness of the treated ear, i.e., $$\frac{\text{thickness of right ear} - \text{thickness of left ear}}{\text{thickness of left ear}} \times 100$$

The vehicle-treated control group was considered to be the maximum burn response within any given experiment. Inhibition or reversal of the burn response due to drug treatment is expressed as a percentage of the control response.

TABLE III

A Dose-Response Comparison of DPE and DPME in the Ear Burn Test
vehicle 90% acetone, 10% IPM: 50 μl/burned ear

| | % inhibition of control response | |
|---|---|---|
| Drug Conc. | DPE | DPME |
| $1 \times 10^{-5}$ M | 25.3 | 31.6 |
| $3 \times 10^{-5}$ | 19.7 | 30.6 |
| $1 \times 10^{-4}$ | 22.9 | 48.4 |
| $3 \times 10^{-4}$ | 31.3 | 41.3 |
| $3 \times 10^{-3}$ | 8.0 | 8.0 |
| $3 \times 10^{-2}$ | −21.5 | −32.6 |

TABLE IV

EAR BURN DATA

| | | | | | | | | | |
|---|---|---|---|---|---|---|---|---|---|
| Control | | | | | | | | | |
| R ear | 15.8 | 15.2 | 14.3 | 17.9 | 18.1 | 17.5 | 17.6 | 18.3 | |
| L ear | 12.2 | 12.0 | 12.2 | 13.0 | 13.9 | 12.7 | 13.5 | 12.9 | $\bar{x} = 31.4 \pm 7.7$ |
| Δ % | 29.5 | 26.7 | 17.2 | 37.7 | 30.2 | 37.8 | 30.4 | 41.9 | |
| Control/Vehicle (90% acetone, 10% IPM) | | | | | | | | | |
| R ear | 18.1 | 20.1 | 18.1 | 18.0 | 17.2 | 20.1 | 16.8 | 17.0 | |
| L ear | 14.4 | 13.8 | 13.9 | 14.4 | 13.1 | 14.0 | 12.2 | 13.0 | $\bar{x} = 32.5 \pm 8.9$ |
| Δ % | 25.7 | 45.7 | 30.2 | 25.0 | 31.3 | 43.6 | 37.7 | 30.8 | |
| DPE | .03 M | | | | | | | | |
| R ear | 17.5 | 21.3 | 18.1 | 18.5 | 20.0 | 17.4 | 15.7 | 18.3 | $\bar{x}$ 39.5 ± 11.4 |
| L ear | 13.2 | 13.6 | 12.6 | 13.5 | 13.1 | 13.5 | 12.7 | 13.0 | −21.5% |
| Δ % | 32.6 | 56.6 | 43.7 | 37.0 | 52.7 | 28.9 | 23.6 | 40.8 | inflammatory |
| DPE | .003 M | | | | | | | | |
| R ear | 18.6 | 19.6 | 19.8 | 16.7 | 16.5 | 17.1 | 13.4 | 17.2 | $\bar{x} = 29.9 \pm 10.8$ |
| L ear | 13.3 | 13.9 | 13.8 | 13.7 | 13.4 | 13.2 | 11.9 | 13.5 | 8% Inhibi- |
| Δ % | 39.8 | 41.0 | 43.5 | 21.9 | 23.1 | 29.5 | 12.6 | 27.4 | tion |
| DPME | .03 M | | | | | | | | |
| R ear | 18.4 | 16.9 | 20.7 | 18.2 | 19.3 | 20.9 | 19.0 | | $\bar{x} = 43.1 \pm 12.4$ |
| L ear | 13.5 | 13.0 | 14.0 | 14.0 | 13.5 | 12.7 | 12.7 | | −32.6% |
| Δ % | 36.3 | 30.0 | 47.9 | 30.0 | 43.0 | 64.6 | 49.6 | | inflammatory |
| DPME | .003 M | | | | | | | | |
| R ear | 19.9 | 15.1 | 18.1 | 17.0 | 17.1 | 15.2 | 14.0 | 16.9 | $\bar{x}$ 29.9 ± 12.2 |
| L ear | 13.7 | 12.4 | 12.7 | 13.4 | 12.1 | 12.9 | 12.4 | 12.9 | 8% Inhibi- |
| Δ % | 45.3 | 21.8 | 42.5 | 26.9 | 41.3 | 17.8 | 12.9 | 31.0 | tion |
| Control | | | | | | | | | |
| R ear | 17.6 | 17.5 | 21.2 | 17.8 | 22.2 | 17.4 | 17.3 | 18.5 | |
| L ear | 13.1 | 12.7 | 13.4 | 13.3 | 14.5 | 12.9 | 12.8 | 13.3 | $\bar{x} = 40.8 \pm 9.4$ |
| Δ % | 34.4 | 37.8 | 58.2 | 33.8 | 53.1 | 34.9 | 35.2 | 39.1 | |
| Control/Vehicle (90% acetone, 10% IPM) | | | | | | | | | |
| R ear | 17.6 | 20.0 | 21.0 | 17.2 | 18.1 | 18.2 | 18.1 | 15.5 | |
| L ear | 12.8 | 12.7 | 13.3 | 13.1 | 13.2 | 13.2 | 12.7 | 12.9 | $\bar{x} = 40.2 \pm 12.6$ |
| Δ % | 37.5 | 57.5 | 57.9 | 31.3 | 37.1 | 37.9 | 42.5 | 20.2 | |
| DPE | .0003 M | | | | | | | | |
| R ear | 15.8 | 16.4 | 18.0 | 18.3 | 17.7 | 16.6 | 15.2 | 16.2 | $\bar{x} = 27.6 \pm 6.9$ |
| L ear | 12.4 | 13.0 | 14.1 | 13.5 | 13.2 | 13.0 | 13.5 | 12.5 | 31.3% Inhi- |
| Δ % | 27.4 | 26.2 | 27.7 | 35.6 | 34.1 | 27.7 | 12.6 | 29.6 | bition |
| DPE | .00003 M | | | | | | | | |
| R ear | 16.4 | 18.2 | 17.5 | 18.1 | 16.8 | 18.5 | 14.5 | 16.0 | $\bar{x} = 32.3 \pm 5.2$ |
| L ear | 12.7 | 13.7 | 13.3 | 12.9 | 12.3 | 13.5 | 11.8 | 12.3 | 19.7% Inhi- |
| Δ % | 29.1 | 32.8 | 31.6 | 40.3 | 36.6 | 37.0 | 22.9 | 30.1 | bition |
| DPME | .0003 M | | | | | | | | |
| R ear | 17.7 | 16.4 | 18.0 | 17.5 | 15.2 | 15.5 | 15.0 | 14.8 | $\bar{x} = 23.6 \pm 7.9$ |
| L ear | 14.5 | 14.0 | 13.0 | 13.3 | 12.4 | 12.5 | 12.8 | 12.8 | 41.3% Inhi- |
| Δ % | 22.1 | 17.1 | 38.5 | 31.6 | 22.6 | 24.0 | 17.2 | 15.6 | bition |
| DPME | .00003 M | | | | | | | | |
| R ear | 15.3 | 17.8 | 16.6 | 16.3 | 15.5 | 15.4 | 16.6 | 16.9 | $\bar{x} = 27.9 \pm 6.2$ |
| L ear | 13.0 | 12.9 | 12.6 | 13.0 | 12.3 | 12.4 | 12.5 | 13.3 | 30.6% Inhi- |
| Δ % | 17.7 | 38.0 | 31.7 | 25.4 | 26.0 | 24.2 | 32.8 | 27.0 | bition |

TABLE IV-continued
EAR BURN DATA

| Control | | | | | | | | | |
|---|---|---|---|---|---|---|---|---|---|
| L ear | 12.2 | 12.0 | 13.8 | 11.7 | 12.2 | 12.0 | 12.1 | | $\bar{x} = 38.8\%$ |
| R ear | 18.4 | 15.9 | 17.5 | 17.6 | 16.5 | 16.7 | 16.5 | | $s = \pm 9.0$ |
| Δ % | 50.8 | 32.5 | 26.8 | 50.4 | 35.2 | 39.2 | 36.4 | | n = 7 |
| Control/Vehicle (90% acetone, 10% IPM) | | | | | | | | | |
| L ear | 12.5 | 12.7 | 13.1 | 12.6 | 12.5 | 12.4 | 12.9 | 11.7 | $\bar{x} = 44.6\%$ |
| R ear | 16.8 | 18.3 | 19.6 | 18.2 | 19.2 | 17.2 | 19.1 | 16.8 | $s = \pm 6.1$ |
| Δ % | 34.4 | 44.1 | 49.6 | 44.4 | 53.6 | 38.7 | 48.1 | 43.6 | n = 8 |
| DPE | 0.0001 M | | | | | | | | |
| L ear | 12.1 | 12.8 | 12.8 | 12.3 | 12.5 | 12.5 | 12.9 | 12.5 | $\bar{x} = 34.4\%$ |
| R ear | 15.9 | 17.3 | 17.4 | 18.3 | 16.6 | 15.8 | 16.4 | 17.2 | $s = \pm 7.1$ |
| Δ % | 31.4 | 35.2 | 35.9 | 48.8 | 32.8 | 26.4 | 27.1 | 37.6 | n = 8 |
| | | | | | | | | 22.9% | inhibition |
| DPE | 0.00001 M | | | | | | | | |
| L ear | 12.6 | 12.4 | 13.0 | 12.1 | 12.4 | 12.7 | 11.6 | 12.5 | $\bar{x} = 33.3\%$ |
| R ear | 17.8 | 15.7 | 16.2 | 15.7 | 18.1 | 16.1 | 14.5 | 18.3 | $s = \pm 9.6$ |
| Δ % | 41.3 | 26.6 | 24.6 | 29.8 | 46.0 | 26.8 | 25.0 | 46.4 | n = 8 |
| | | | | | | | | 25.3% | inhibition |
| DPME | 0.0001 M | | | | | | | | |
| L ear | 11.8 | 11.9 | 12.1 | 11.9 | 11.7 | 12.0 | 11.8 | 12.0 | $\bar{x} = 23.0\%$ |
| R ear | 14.0 | 14.7 | 13.6 | 14.5 | 15.4 | 14.7 | 14.9 | 15.3 | $s = \pm 5.8$ |
| Δ % | 18.6 | 23.5 | 12.4 | 21.8 | 31.6 | 22.5 | 26.3 | 27.5 | n = 8 |
| | | | | | | | | 48.4% | inhibition |
| DPME | 0.00001 M | | | | | | | | |
| L ear | 12.5 | 12.2 | 11.8 | 11.5 | 12.0 | 12.2 | 12.7 | 12.3 | $\bar{x} = 30.5\%$ |
| R ear | 16.3 | 16.5 | 13.8 | 14.1 | 17.0 | 14.7 | 17.8 | 16.8 | $s = \pm 9.4$ |
| Δ % | 30.4 | 35.2 | 16.9 | 22.6 | 41.7 | 20.5 | 40.2 | 36.6 | n = 8 |
| | | | | | | | | 31.6% | inhibition |

From the foregoing, it will be appreciated that the prodrug derivatives according to the inventor exhibit all of the biological and therapeutic activity of their "parent" sympathominetic amines, whether for the treatment of glaucoma, bronchial asthma, nasal decongestion, allergies, itching, inflammation, or any other disease state or condition responsive to active agents displaying synpathominetic activity, while at the same time being characterized by enhanced bioavailability and physiological availability, enhanced resistance to deterioration by air and light and to chemical attack, and even the ability to elicit the same pharmacological response as the parent drug form, but at lower dosages.

The dose of the prodrug administered, whether orally, topically, inhalation spray or mist, intravenous or ophthalmic solution, ointment, or the like, and whether a single dose or a daily dose, will, of course, vary with the needs of the individual. However, the dosage administered is not subject to definite bounds, but will usually be an effective amount, or the equivalent on a molar basis of the pharmacologically active form produced upon the metabolic release of the active drug to achieve its desired and physiological effect. See *Physicians' Desk Reference*, 31 (1977). Moreover, for any of the broad spectrum of dosage forms into which the subject produced can be formulated see *Remington's Pharmaceutical Sciences*, 14th Edition (1970).

While the invention has been described in terms of various preferred embodiments, the skilled artisan will appreciate that various modifications, substitutions, omissions and changes may be made without departing from the spirit thereof. Accordingly, it is intended that the scope of the present invention be limited solely by the scope of the following claims.

What is claimed is:

1. A compound selected from the group consisting of those having (i) the structural formula (I):

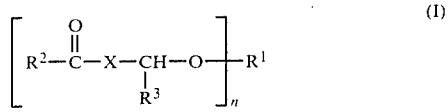

wherein X is O, S or $NR^5$; n is 1 or 2; $R^1$ is the monodehydroxylated residue of a phenolic, nuclear dihydroxy natural sympathetic or sympathomimetic amine when n is 1, and the didehydroxylated residue of a phenolic, nuclear dihydroxy natural sympathetic or sympathomimetic amine when n is 2, said natural sympathetic or sympathomimetic amine comprising a basic nucleus selected from the group consisting of epinephrine, norepinephrine, isoproterenol, isoetharine, protochylol, adrenalone, dihydroxyphenylaminobutanol, nordefrin, colterol, fenoterol, metaproterenol, terbutaline, carbidopa and methyldopa; $R^2$ is selected from the group consisting of straight or branched chain alkyl having from 1 to 20 carbon atoms; aryl having from 6 to 10 carbon atoms; cycloalkyl having from 3 to 8 carbon atoms; alkenyl having from 2 to 20 carbon atoms; cycloalkenyl having from 4 to 8 carbon atoms; alkynyl having from 2 to 20 carbon atoms; aralkyl, alkaryl, aralkenyl, aralkynyl, alkenylaryl, alkynylaryl loweracyloxyalkyl, and carboxyalkyl, wherein alkyl, aryl, alkenyl and alkynyl are as defined above; and mono- or poly-substituted derivatives of the above, each of said substituents being selected from the group consisting of lower alkyl, lower alkoxy, lower acyl, lower acyloxy, halo, haloloweralkyl, cyano, carbethoxy, loweralkylthio, amino, nitro, loweralkylamino, diloweralkylamino, carboxyl, carbamyl, loweralkylcarbamyl, diloweralkylcarbamyl and

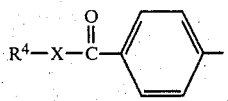

wherein $R^4$ is hydrogen or alkyl having from 1 to 10 carbons; $R^3$ is hydrogen, $R^2$, lower acyl, cyano, haloloweralkyl, carbamyl, loweralkylcarbamyl, diloweralkylcarbamyl, $-CH_2ONO_2$ and $-CH_2OCOR^2$; $R^5$ is hydrogen or lower alkyl; (ii) the structural formula (II):

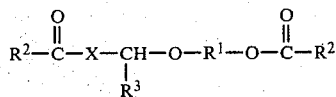

wherein X, $R^2$ and $R^2$ and $R^3$ are as defined above and $R^1$ is the didehydroxylated residue of a phenolic, nuclear dihydroxy natural sympathetic or sympathomimetic amine as defined above; and (iii) the non-toxic, pharmaceutically acceptable salts thereof.

2. A compound as defined by claim 1, having the structural formula (i)(I), wherein n is 2.

3. A compound as defined by claim 1, having the structural formula (i)(I), wherein n is 1.

4. A compound as defined by claim 1, having the structural formula (ii)(II).

5. A compound as defined by claim 1, having the structural formula (iii)(I), wherein n is 2.

6. A compound as defined by claims 2 or 3 wherein X is O.

7. A compound as defined by claims 2 or 3, wherein X is S.

8. A compound as defined by claims 2 or 3, wherein X is $NR^5$.

9. A compound as defined by claim 1, wherein $R^2$ is straight or branched chain alkyl having from 1 to 20 carbon atoms.

10. A compound as defined by claim 1, wherein $R^2$ is aryl having from 6 to 10 carbon atoms.

11. A compound as defined by claim 1, wherein $R^2$ is cycloalkyl having from 3 to 8 carbon atoms.

12. A compound as defined by claim 1, wherein $R^2$ is alkenyl having from 2 to 20 carbon atoms.

13. A compound as defined by claim 1, wherein $R^2$ is cycloalkenyl having from 4 to 8 carbon atoms.

14. A compound as defined by claim 1, wherein $R^2$ is alkynyl having from 2 to 20 carbon atoms.

15. A compound as defined by claim 8, wherein $R^5$ is hydrogen.

16. A compound as defined by claim 8, wherein $R^5$ is lower alkyl.

17. A compound as defined by claim 1, wherein $R^3$ is hydrogen.

18. A compound as defined by claim 1, wherein $R^3$ is alkyl.

19. A compound as defined by claim 1, wherein $R^3$ is haloloweralkyl.

20. A compound as defined by claim 19, wherein $R^3$ is trifluoromethyl.

21. A sympathomimetically effective composition of matter comprising a sympathomimetically effective amount of a compound as defined by claim 1, and a pharmaceutically effective carrier therefor.

22. The method of eliciting a sympathomimetic response in a warm-blooded animal, which comprises administering to such animal a sympathomimetically effective amount of a compound as defined by claim 1.

23. A compound as defined by claim 1, said natural sympathetic or sympathomimetic amine comprising an epinephrine basic nucleus.

24. A compound as defined by claim 1, said natural sympathetic or sympathomimetic amine comprising a norepinephrine basic nucleus.

25. A compound as defined by claim 1, said natural sympathetic or sympathomimetic amine comprising an isoproterenol basic nucleus.

26. A compound as defined by claim 1, said natural sympathetic or sympathomimetic amine comprising an adrenalone basic nucleus.

27. A compound as defined by claim 1, said natural sympathetic or sympathomimetic amine comprising an isoetharine basic nucleus.

28. A compound as defined by claim 1, said natural sympathetic or sympathomimetic amine comprising a protochylol basic nucleus.

29. A compound as defined by claim 1, said natural sympathetic or sympathomimetic amine comprising a nordefrin basic nucleus.

30. A compound as defined by claim 1, said natural sympathetic or sympathomimetic amine comprising a dihydroxyphenylaminobutanol basic nucleus.

31. A compound as defined by claim 1, said natural sympathetic or sympathomimetic amine comprising a colterol basic nucleus.

32. A compound as defined by claim 1, said natural sympathetic or sympathomimetic amine comprising a fenoterol basic nucleus.

33. A compound as defined by claim 1, said natural sympathetic or sympathomimetic amine comprising a metaproterenol basic nucleus.

34. A compound as defined by claim 1, said natural sympathetic or sympathomimetic amine comprising a terbutaline basic nucleus.

35. A compound as defined by claim 1, said natural sympathetic or sympathomimetic amine comprising a carbidopa basic nucleus.

36. A compound as defined by claim 1, said natural sympathetic or sympathomimetic amine comprising a methyldopa basic nucleus.

* * * * *